United States Patent
Machhammer et al.

(10) Patent No.: US 6,426,433 B1
(45) Date of Patent: Jul. 30, 2002

(54) METHOD FOR PRODUCING ACROLEIN AND/OR ACRYLIC ACID FROM PROPANE

(75) Inventors: Otto Machhammer, Mannheim; Andreas Tenten, Maikammer; Harald Jachow, Bensheim; Susanne Haupt, Offenbach; Heiko Arnold; Signe Unverricht, both of Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/763,225

(22) PCT Filed: Aug. 10, 1999

(86) PCT No.: PCT/EP99/05793

§ 371 (c)(1),
(2), (4) Date: Feb. 20, 2001

(87) PCT Pub. No.: WO00/10961

PCT Pub. Date: Mar. 2, 2000

(30) Foreign Application Priority Data

Aug. 19, 1998 (DE) .......................................... 198 37 517

(51) Int. Cl.[7] .......................... C07C 51/16; C07C 51/42
(52) U.S. Cl. ...................... 562/545; 562/545; 562/600
(58) Field of Search ................... 562/545, 600

(56) References Cited

U.S. PATENT DOCUMENTS

| 3,161,670 A | 12/1964 | Adams et al. |
| 3,798,283 A | 3/1974 | Bitar et al. |
| 4,066,704 A | 1/1978 | Harris et al. |
| 4,532,365 A | 7/1985 | Khoobiar |
| 5,183,936 A | 2/1993 | Etzkorn et al. |
| 5,198,578 A | 3/1993 | Etzkorn et al. |

FOREIGN PATENT DOCUMENTS

| CN | 11 053 52 | 7/1995 |
| DE | 20 58 054 | 6/1971 |
| DE | 33 13 573 | 10/1983 |
| DE | 195 30 454 | 2/1997 |
| DE | 196 22 331 | 12/1997 |
| EP | 0 117 446 | 9/1984 |
| EP | 0 293 224 | 11/1988 |
| WO | WO 97/36849 | 10/1997 |

OTHER PUBLICATIONS

Y.–C. Kim, et al., Applied Catalysis, vol. 70, pps. 175–187, "Selective Oxidation of Propane Involving Homogeneous and Heterogeneous Steps Over Multicomponent Metal Oxide Catalysts," 1991.

Y.–C. Kim, et al., Catalysis Today, vol. 13, pps. 673–678, "Catalytic (AMM)Oxidation of Propane With Molecular Oxygen Over Complex Metal Oxides: Involvement of Homogeneous Reaction in Gas Phase," 1992.

*Primary Examiner*—Paul J. Killos
*Assistant Examiner*—Farhad Forohar
(74) *Attorney, Agent, or Firm*—Oblon, Spivak, McClelland, Maier & Neustadt, P.C.

(57) ABSTRACT

In a process for the preparation of acrolein and/or acrylic acid from propane, the propane is subjected, in a first reaction stage, to a partial oxydehydrogenation with molecular oxygen under homogeneous and/or heterogeneous catalysis to give propene and the product gas mixture formed in the first reaction stage is then used for the preparation of acrolein and/or acrylic acid by gas-phase catalytic propene oxidation.

20 Claims, 2 Drawing Sheets

METHOD FOR PRODUCING ACROLEIN AND/OR ACRYLIC ACID FROM PROPANE

BACKGROUND OF THE INVENTION

1. Field of the Invention

Preparation of acrolein and/or acrylic acid from propane The present invention relates to a process for the preparation of acrolein and/or acrylic acid from propane, in which, in a first reaction zone, the propane is subjected to a partial oxydehydrogenation with molecular oxygen under homogeneous and/or heterogeneous catalysis to give propene, and the propene-containing product gas mixture formed in the first reaction zone is fed, without separating off a component of the product gas mixture, into at least one further reaction zone and, in this at least one further reaction zone, the propene contained in the product gas mixture of the first reaction zone, together with all components of the product gas mixture of the first reaction zone, is subjected to a gas-phase catalytic oxidation to acrolein and/or acrylic acid, acrolein and/or acrylic acid and water contained in the product gas mixture of the gas-phase catalytic oxidation are separated from said mixture, and the unconverted propane contained in the remaining residual gas stream is recycled as a component of the residual gas stream to the first reaction zone.

2. Discussion of the Background

Acrolein and acrylic acid are important intermediates which are used, for example, in the preparation of active ingredients and polymers.

The process predominantly used at present on an industrial scale for the production of acrolein and/or acrylic acid is the gas-phase catalytic oxidation of propene (e.g. EP-A 575 897), the propene predominantly being produced as a byproduct of ethylene production by steam cracking of naphtha.

Since the other fields of use of propene, for example the preparation of polypropylene, are constantly expanding, it would be advantageous to have a competitive process for the preparation of acrolein and/or acrylic acid which can be used on an industrial scale and whose raw material base is not propene but, for example, the propane occurring naturally in large quantities as the component of natural gas.

U.S. Pat. No. 3,798,283 discloses that propane can be homogeneously oxydehydrogenated to propene in the presence of molecular oxygen at elevated temperatures. Suitable oxygen sources are both pure oxygen and mixtures of oxygen and inert gas.

DE-A 20 58 054 and DE-A 1 95 30 454 disclose that the oxydehydrogenation of propane to propene can also be carried out under heterogeneous catalysis.

U.S. Pat. No. 3,161,670, EP-A 117 446 and DE-A 33 13 573 relate to processes for the preparation of acrolein and/or acrylic acid in which propane is first subjected to dehydrogenation under heterogeneous catalysis in the absence of oxygen to give propene.

The propene-containing product mixture is then subjected to a gas-phase oxidation under heterogeneous catalysis. However, the disadvantage of this procedure is that the catalyst required for the nonoxidative dehydrogenation of propane is relatively rapidly deactivated by carbon deposits and must therefore be frequently regenerated. A further disadvantage of this procedure is the hydrogen formation associated with the nonoxidative propane dehydrogenation.

It is true that DE-A 33 13 573 mentions the possibility in principle of coupling oxidative dehydrogenation of propane to propene with a subsequent propene oxidation under heterogeneous catalysis. However, it contains no further information on carrying out such a process.

EP-A 293 224, U.S. Pat. No. 5,198,578 and U.S. Pat. No. 5,183,936 state that a high $N_2$ content in the diluent gas of the catalytic gas-phase oxidation of propene to acrolein and/or acrylic acid is disadvantageous. EP-A 293 224 furthermore suggests combining the oxidative dehydrogenation of propane to propene and the catalytic gas-phase oxidation of propene with one another for the preparation of acrolein and/or acrylic acid.

In Catalysis Today 13 (1992), 673 to 678, Moro-oka et al. combine in laboratory experiments a homogeneous oxidative dehydrogenation of propane to propene with a subsequent oxidation of the dehydrogenation product mixture under heterogeneous catalysis to acrolein and/or acrylic acid. The corresponding combination of processes is recommended by Moro-oka et al. in Applied Catalysis 70 (2) (1991), 175 to 187. In line with the recommendation of EP-A 293224, of U.S. Pat. No. 5,198,578 and of U.S. Pat. No. 5,183,936, Moro-oka et al. use either pure molecular oxygen or air depleted with respect to nitrogen in all cases as an oxygen source for the oxydehydrogenation stage. For the latter case, Moro-oka envisages absolutely no separation, in the further course of his process, of nitrogen introduced into the process.

CN-A 1105352 likewise discloses a homogeneous oxidative dehydrogenation of propane to propene with a subsequent oxidation of the dehydrogenation product mixture under heterogeneous catalysis to give acrolein and/or acrylic acid. Since the process in CN-A 1105352 is a procedure to be carried out on the industrial scale, CN-A 1105352, following the recommendation of EP-A 293 224, U.S. Pat. No. 5,198,578 and U.S. Pat. No. 5,183,936, uses exclusively pure molecular oxygen as the oxygen source.

WO 97/36849 relates to the combination of the catalytic oxidative dehydrogenation of propane to propene with a subsequent oxidation of the dehydrogenation product mixture under heterogeneous catalysis to give acrolein and/or acrylic acid in an industrial embodiment. Although WO 97/36849 does not rule out the use of nitrogen-containing oxygen (e.g. air) as a source of the molecular oxygen required in the oxydehydrogenation, it advises against said use. Moreover, WO 97/36849 envisages merely a purge of recycled gas and not removal of components from the recycled gas for the case of a continuous procedure with gas recycling for suppressing an undesired increase in the concentration of disadvantageous components of the reaction gas mixture.

For cost-efficiency reasons, essentially only air is suitable as a starting material for the molecular oxygen source for industrial gas-phase oxidations.

Against this background, the abovementioned procedures, in particular the continuous execution thereof, are or is disadvantageous in that, owing to the similarity of $O_2$ and $N_2$ starting from air, the sole measure of a prior nitrogen/oxygen separation for the preparation of pure oxygen or of air depleted with respect to nitrogen, if required in combination with a recycled gas purge, for limiting the nitrogen content in the gas-phase oxidation of the propene contained in the dehydrogenation product mixture is very energy-consuming.

SUMMARY OF THE INVENTION

It is an object of the present invention to provide a process for the preparation of acrolein and/or acrylic acid from propane, in which, in a first reaction zone, the propane is subjected to a partial oxydehydrogenation with molecular oxygen under homogeneous and/or heterogeneous catalysis to give propene, and the propene-containing product gas mixture formed in the first reaction zone is fed, without separating off a component of the product gas mixture, into at least one further reaction zone and, in this at least one further reaction zone, the propene contained in the product gas mixture of the first reaction zone, together with all components of the product gas mixture of the first reaction zone, is subjected to a gas-phase catalytic oxidation to acrolein and/or acrylic acid, acrolein and/or acrylic acid and water contained in the product gas mixture of the gas-phase catalytic oxidation are separated from said mixture and the unconverted propane contained in the remaining residual gas stream is recycled as a component of the residual gas stream to the first reaction zone, and in which the limitation of the nitrogen content in the propene oxidation stage is effected in a less energy-consuming manner than in the prior art.

We have found that this object is achieved by a process for the preparation of acrolein and/or acrylic acid from propane, in which, in a first reaction zone, the propane is subjected to a partial oxydehydrogenation with molecular oxygen under homogeneous and/or heterogeneous catalysis to give propene, and the propene-containing product gas mixture formed in the first reaction zone is fed, without separating off a component of the product gas mixture, into at least one further reaction zone and, in this at least one further reaction zone, the propene contained in the product gas mixture of the first reaction zone, together with all components of the product gas mixture of the first reaction zone, is subjected to a gas-phase catalytic oxidation to acrolein and/or acrylic acid, acrolein and/or acrylic acid and water contained in the product gas mixture of the gas-phase catalytic oxidation are separated from said mixture, and the unconverted propane contained in the remaining residual gas stream is recycled as a component of the residual gas stream to the first reaction zone, wherein the molecular oxygen required in the first reaction zone and differing from recycled oxygen is added as nitrogen-containing modified air to the reaction gas starting mixture fed to the first reaction zone, with the proviso that the nitrogen content of the modified air is less than, and the oxygen content of the modified air greater than, the corresponding contents of air, and, before the recycling of the residual gas stream to the first reaction zone, at least a part of the molecular nitrogen contained in the residual gas stream is separated from the residual gas stream.

DESCRIPTION OF THE PREFERRED EMBODIMENTS

Detailed research has shown that the advantageousness in principle of the novel procedure over the most closely related processes of the prior art is due to the fact that in particular the chemical bonding of the molecular oxygen which takes place in the oxidative dehydrogenation of the propane using a nitrogen-containing oxygen source implicitly performs a part of separation work to be performed for separating atmospheric nitrogen and atmospheric oxygen. The same applies to the subsequent oxidation stages. The difference between the resulting, oxygen-containing, polar compounds (e.g. acrylic acid, acrolein, $H_2O$, CO, $CO_2$) and $N_2$ is subsequently more pronounced than the difference between $N_2$ and $O_2$, which is why their separation from nitrogen, in contrast to a nitrogen/oxygen separation, is possible with very much less effort. The same applies to a separation of $N_2$ from the other possible components of the residual gas stream mainly comprising $N_2$ and propane, since both the difference between propane and $N_2$ and the difference between $N_2$ and the other possible components of the residual gas stream are very much greater than the difference between $O_2$ and $N_2$. As a rule, separation of $N_2$ by rectification with comparatively less effort is possible.

If, in the novel process, the first reaction zone is designed as a homogeneous oxydehydrogenation, this can in principle be carried out, for example, as described in U.S. Pat. No. 3,798,283, CN-A 1 105 352, Applied Catalysis 70 (2) (1991), 175 to 187, Catalysis Today 13 (1992), 673 to 678, and the prior application DE-A 1 96 22 331, except for the fact that, according to the invention, air to be used as the oxygen source (apart from recycled oxygen gas).

The temperature of the homogeneous oxydehydrogenation is expediently chosen to be from 300 to 700° C., preferably from 400 to 600° C., particularly preferably from 400 to 500° C. The operating pressure may be from 0.5 to 100 bar or from 1 to 50 bar. Frequently, it is from 1 to 20 bar or from 1 to 10 bar.

The residence time of the reaction gas mixture under oxydehydrogenation conditions is usually 0.1 or 0.5 to 20, preferably 0.1 or 0.5 to 5, seconds. The homogeneous oxydehydrogenation can be carried out, for example, in a separate reactor. The reactor used may be, for example, a tube furnace or a tube-bundle reactor, such as a countercurrent tube furnace with stack gas as heating medium or a tube-bundle reactor with salt melt as heating medium.

The propane to oxygen ratio in the reaction gas starting mixture to be used for a homogeneous oxydehydrogenation may be from 0.5:1 to 40:1. It is advantageous according to the invention if the molar ratio of propane to molecular oxygen in the reaction gas starting mixture is $\leq 6:1$ or $\leq 5:1$. As a rule, the abovementioned ratio is $\geq 1:1$ or $\geq 2:1$. The nitrogen content of the reaction gas starting mixture is as a rule a consequence of the abovementioned requirement since said starting mixture usually comprises essentially no further gases apart from propane and air. However, it is of course also possible for the reaction gas starting mixture to comprise further, essentially inert components, such as $H_2O$, $CO_2$, CO, $N_2$, noble gases and/or propene. Propene as a component of the reaction gas starting mixture is added, for example, when the starting propane used is the $C_3$ fraction from the refinery or the $C_3$ fraction from the light hydrocarbons of the oil field, which may have a propene content of up to 10% by weight. Furthermore, it may originate from the gas recycling required according to the invention. Components recycled to the oxydehydrogenation are referred to in this publication very generally as recycled gas. As a result of gas recycling, for example, the nitrogen content of the reaction gas starting mixture may be up to 60 mol % or up to 50 mol %. The novel gas recycling may also result in the reaction gas starting mixture having up to 5 mol % of gases such as CO, $CO_2$, ethene and $H_2O$ in the continuous procedure. It is advantageous for a homogeneous oxidative dehydrogenation of propane to propene if the ratio of the surface area of the reaction space to the volume of the reaction space is very small. This is a consequence of the free radical mechanism of the homogeneous oxidative propane dehydrogenation, since reaction space surfaces do in fact generally act as free radical acceptors. Particularly advantageous surface materials are aluminas, quartz glass, borosilicates, stainless steel and aluminum.

If, in the novel process, the first reaction stage is designed as an oxydehydrogenation under heterogeneous catalysis, this can in principle be carried out, for example, as described in U.S. Pat. No. 4,788,371, CN-A 1073893, Catalysis Letters 23 (1994), 103–106, W. Zhang, Gaodeng Xuexiao Huaxue, 14 (1993), 566, Z. Huang, Shiyou Huagong, 21 (1992), 592, WO 97/36849, DE-A 1 97 53 817, U.S. Pat. No. 3,862,256, U.S. Pat. No. 3,887,631, DE-A 1 95 30 454, U.S. Pat. No. 4,341,664, J. of Catalysis 167 (1997), 560–569, J. of Catalysis 167 (1997), 550–559, Topics in Catalysis 3 (1996), 265–275, U.S. Pat. No. 5,086,032, Catalysis Letters 10 (1991), 181–192, Ind. Eng. Chem. Res. 35 (1996), 14–18, U.S. Pat. No. 4,255,284, Applied Catalysis A: General 100 (1993), 111–130, J. of Catalysis 148 (1994), 56–67, V. Cortes Corberan and S. Vic Bellon (Editors), New Developments in Selective Oxidation II, 1994, Elsevier Science B. V., pages 305–313, 3rd World Congress on Oxidation Catalysis, R. K. Grasselli, S. T. Oyama, A. M. Gaffney and J. E. Lyons (Editors), 1997, Elsevier Science B.V., page 375 et seq., except that, according to the invention, air is to be used as the oxygen source (apart from recycled oxygen gas). In particular, all oxydehydrogenation catalysts stated in the abovementioned publications may be used. The statements made in connection with the abovementioned publications also apply to:

a) Otsuka, K.; Uragami, Y.; Komatsu, T.; Hatano, M. in Natural Gas Conversion, Stud. Surf. Sci. Catal.; Holmen A.; Jens, K.-J.; Kolboe, S., Eds.; Elsevier Science: Amsterdam, 1991; Vol. 61, p 15;

b) Seshan, K.; Swaan, H. M.; Smits, R. H. H.; van Ommen, J. G.; Ross, J. R. H. in New Developments in Selective Oxidation; Stud. Surf. Sci. Catal.; Centi, G.; Trifiro, F., Eds.; Elsevier Science: Amsterdam 1990; Vol. 55, p 505;

c) Smits, R. H. H.; Seshan, K.; Ross, J. R. H. in New Developments in Selective Oxidation by Heterogeneous Catalysis; Stud. Surf. Sci. Catal.; Ruiz, P.; Delmon, B., Eds.; Elsevier Science: Amsterdam, 1992 a; Vol. 72, p 221;

d) Smits, R. H. H.; Seshan, K.; Ross, J. R. H. Proceedings, Symposium on Catalytic Selective Oxidation, Washington D.C.; American Chemical Society: Washington, D.C., 1992 b; 1121;

e) Mazzocchia, C.; Aboumrad, C.; Daigne, C.; Tempesti, E.; Herrmann, J. M.; Thomas, G. Catal. Lett. 10 (1991), 181;

f) Bellusi, G.; Conti, G.; Perathonar, S.; Trifiro, F. Proceedings, Symposium on Catalytic Selective Oxidation, Washington, DC; American Chemical Society: Washington, D.C., 1992; p 1242;

g) Ind. Eng. Chem. Res. 35 (1996), 2137–2143 and h) Symposium on Heterogeneous Hydrocarbon Oxidation Presented before the Division of Petroleum Chemistry, Inc. 211 th National Meeting, American Chemical Society New Orleans, La., Mar. 24–29, 1996.

Oxydehydrogenation catalysts which are particularly suitable according to the invention are the multimetal oxide materials or multimetal oxide catalysts A of DE-A 1 97 53 817, the multimetal oxide materials or multimetal oxide catalysts A stated as being preferred in the abovementioned publication being very particularly advantageous, i.e. particularly suitable active materials are multimetal oxide materials of the formula I $$M^1{}_a Mo_{1-b} M^2{}_b O_x \qquad (I),$$

where $M^1$ is Co, Ni, Mg, Zn, Mn and/or Cu, $M^2$ is W, V, Te, Nb, P, Cr, Fe, Sb, Ce, Sn and/or La, a is from 0.5 to 1.5, b is from 0 to 0.5 and x is a number which is determined by the valency and frequency of the elements other than oxygen in I.

In principle, active materials I suitable according to the invention can be prepared in a simple manner by producing, from suitable sources of their elemental constituents, a very intimate, preferably finely divided dry blend having a composition corresponding to their stoichiometry, and calcining said dry blend at from 450 to 1000° C. The calcination can be carried out both under inert gas and under an oxidizing atmosphere, e.g. air (mixture of inert gas and oxygen) and also under a reducing atmosphere (e.g. mixture of inert gas, oxygen and $NH_3$, CO and/or $H_2$). The duration of calcination may be from a few minutes to a few hours and usually decreases with the temperature. Suitable sources of the elemental constituents of the multimetal oxide active materials I are those compounds which are already oxides and/or those compounds which can be converted into oxides by heating, at least in the presence of oxygen.

In addition to the oxides, suitable starting compounds of this type are in particular halides, nitrates, formates, oxalates, citrates, acetates, carbonates, amine complex salts, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate, which decompose and/or can be decomposed at the latest during the subsequent calcination into compounds escaping completely in gaseous form, can additionally be incorporated into the intimate dry blend). The intimate mixing of the starting compounds for the preparation of multimetal oxide materials I can be carried out in dry or in wet form. If it is effected in dry form, the starting compounds are expediently used as finely divided powders and, after mixing and, if required, compaction, are subjected to calcination. However, the intimate mixing is preferably effected in wet form. Usually, the starting compounds are mixed with one another in the form of an aqueous solution and/or suspension.

Particularly intimate dry blends are obtained in the dry method described when exclusively dissolved sources of the elemental constituents are used as starting materials. The preferably used solvent is water. The aqueous material obtained is then dried, the drying process preferably being carried out by spray-drying the aqueous mixture with outlet temperatures of from 100 to 150° C. Particularly suitable starting compounds of Mo, V, W and Nb are their oxo compounds (molybdates, vanadates, tungstates and niobates) or the acids derived from these. This applies in particular to the corresponding ammonium compounds (ammonium molybdate, ammonium vanadate, ammonium tungstate).

For the novel process, the multimetal oxide materials I can be used both in powder form and with specific catalyst geometries, it being possible to carry out shaping before or after the final calcination. For example, unsupported catalysts can be prepared from the powder form of the active material or its uncalcined precursor material by compaction to the desired catalyst geometry (for example by pelleting or extrusion), it being possible, if required, to add assistants, such as graphite or stearic acid as lubricants and/or molding assistants and reinforcing materials, such as microfibers of glass, asbestos, silicon carbide or potassium titanate. Suitable unsupported catalysts are, for example, solid cylinders or hollow cylinders having an external diameter and a length of from 2 to 10 mm. In the case of the hollow cylinders, a wall thickness of from 1 to 3 mm is expedient. Suitable geometries for hollow cylinders are, for example, 7 mm×7 mm×4 mm or 5 mm×3 mm×2 mm or 5 mm×2 mm×2 mm (in each case length×external diameter×internal diameter).

of course, the unsupported catalyst may also have spherical geometry, where the sphere diameter may be from 2 to 10 mm.

Of course, the shaping of the pulverulent active material or of its pulverulent, uncalcined precursor material can also be effected by application to preshaped inert catalyst supports. The coating of the supports for the preparation of coated catalysts is carried out as a rule in a suitable rotatable container, as disclosed, for example, in DE-A 2909671 or in EP-A 293859. Expediently, for coating the supports, the powder material to be applied can be moistened and, after application, for example by means of hot air, can be dried again. The coat thickness of the powder material applied to the support is expediently chosen to be from 50 to 500 $\mu$m, preferably from 150 to 250 $\mu$m.

The support materials used may be conventional porous or nonporous aluminas, silica, thorium dioxide, zirconium dioxide, silicon carbide or silicates, such as magnesium silicate or aluminum silicate. The supports may have a regular or irregular shape, regularly shaped supports having pronounced surface roughness, for example spheres or hollow cylinders, being preferred. The use of essentially nonporous, spherical steatite supports which have a rough surface and whose diameter is from 1 to 8 mm, preferably from 4 to 5 mm, is suitable.

The reaction temperature of the oxydehydrogenation of the propane under heterogeneous catalysis is expediently chosen to be from 300 to 600° C., frequently from 350 to 500° C. An operating pressure of from 0.5 to 10 bar or from 1 to 10 bar or from 1 to 5 bar is recommended. Operating pressures above 1 bar, for example from 1.5 to bar, have proven advantageous. As a rule, the oxydehydrogenation of the propane under heterogeneous catalysis is carried out over a fixed catalyst bed. The latter is expediently poured into the tubes of a tube-bundle reactor, as described, for example, in EP-A 700 893 and in EP-A 700 714 and in the literature cited in these publications. This can be effected, for example, in a separate reactor. The average residence time of the reaction gas mixture in the catalyst bed is usually from 0.5 to 20 seconds. The propane to oxygen ratio in the reaction gas starting mixture to be used for the propane oxydehydrogenation under heterogeneous catalysis may be, according to the invention, from 0.5:1 to 40:1. It is advantageous according to the invention if the molar ratio of propane to molecular oxygen in the reaction gas starting mixture is $\leq$6:1 or $\leq$5:1. As a rule, the abovementioned ratio is $\geq$1:1 or 2:1. The nitrogen content of the reaction gas starting mixture is as a rule a consequence of the abovementioned requirement, since the reaction gas starting mixture usually comprises essentially no further gases apart from propane and air. However, the reaction gas starting mixture can of course also comprise further, essentially inert components, such as $H_2O$, $CO_2$, CO, $N_2$, noble gases and/or propene. Propene is added as a component of the reaction gas starting mixture, for example, when the starting propane used is the $C_3$ fraction from the refinery or the $C_3$ fraction from the light hydrocarbons of the oil field, which may have a propene content of up to 10% by weight. Furthermore, it may be a consequence of the gas recycling required according to the invention. As a result of gas recycling, for example, the nitrogen content of the reaction gas starting mixture of the propane oxydehydrogenation under heterogeneous catalysis in the novel process may be up to 60 mol % or up to 50 mol % if said process is carried out continuously. The novel gas recycling may also result in the reaction gas starting mixture having up to mol % of gases such as CO, $CO_2$, ethane, methane, ethene and/or $H_2O$ in the continuous procedure.

The modified air to be used according to the invention as the oxygen source may contain, for example, from $\geq$0.05 to >78% by volume or from $\geq$0.1 to $\geq$75% by volume of $N_2$, i.e. the nitrogen content of the modified air to be used according to the invention as the oxygen source may be from $\geq$1 to $\leq$70% by volume or from $\geq$5 to $\leq$60% by volume or from $\geq$10 to $\leq$50% by volume or from $\geq$15 to $\leq$40% by volume or from $\geq$20 to $\leq$30% by volume.

Accordingly, the oxygen content of the modified air to be used according to the invention as the oxygen source may be from <20.95 to 99.95% by volume or from $\geq$25 to $\leq$99.9% by volume or from $\geq$30 to $\leq$99% by volume or from $\geq$40 to $\leq$95% by volume or from $\geq$50 to $\leq$90% by volume or from $\geq$60 to $\leq$85% by volume or from $\geq$70 to $\leq$80% by volume.

In addition to oxygen and nitrogen, the modified air to be used according to the invention may also contain the other components otherwise present in air usually in small amounts, such as noble gases, carbon dioxide, water vapor, etc. However, the abovementioned components may of course also have been separated off partially or completely in the modification.

The modified air to be used according to the invention as the oxygen source can be most easily produced, for example, by fractional distillation of air, preferably under pressure. It is of course also possible to use the processes of EP-A 848 981 and EP-A 848 639.

Both the $O_2$ conversion of the homogeneous oxidative propane dehydrogenation and that of the catalytic oxidative propane dehydrogenation in the novel process (with a single pass) may be $\geq$50 mol % or $\geq$70 mol %, i.e. the abovementioned $O_2$ conversion may be $\geq$75 mol % or $\geq$80 mol % or $\geq$85 mol % or $\geq$90 mol % or $\geq$95 mol % or $\geq$97 mol % or $\geq$99 mol %.

Frequently, the $O_2$ conversion of both the homogeneous as well as the catalytic oxidative propane dehydrogenation in the novel process (with a single pass) is $\geq$70 mol %. Of course, homogeneous and catalytic propane oxydehydrogenation can also be used in combination. According to the invention, the propane oxydehydrogenation product gas mixture containing propene and unconverted propane (as a rule it contains $CO_2$, CO, $H_2O$, $N_2$, $O_2$, ethane, ethene, methane, acrolein, acrylic acid, ethylene oxide, butane, acetic acid, formaldehyde, formic acid, propylene oxide and butene as further components) is passed directly into at least one further reaction zone in order to subject the propene contained therein to a catalytic gas-phase oxidation to acrolein and/or acrylic acid.

The abovementioned gas-phase catalytic propene oxidation can be carried out, for example, as described in the prior art, for example in WO 97/36849 or CN-A 1105352. Of course, this gas-phase catalytic propene oxidation can also be effected as described in EP-A 117146, U.S. Pat. No. 5,198,578 or U.S. Pat. No. 5,183,936. It can however also be carried out analogously to DE-A 3313573, CA-A 1217502, U.S. Pat. No. 3,161,670 or U.S. Pat. No. 4,532,365.

The gas-phase catalytic oxidative reaction of the propene contained in the propane oxydehydrogenation product gas mixture to acrolein and/or acrylic acid can be carried out, for example, in one subsequent oxidation zone or in two subsequent oxidation zones. The unconverted propane accompanying the propene, and any noble gas, CO, $CO_2$ and other low molecular weight organic compounds, e.g. other lower hydrocarbons, present in addition to $N_2$ and $H_2O$ act essentially as inert diluent gas. Where acrylic acid is the desired product, as a rule two gas-phase catalytic oxidation zones will follow the oxydehydrogenation, although the prior art also discloses one-stage gas-phase catalytic oxidations of propene to acrylic acid. If acrolein is the desired product, as a rule only one gas-phase catalytic oxidation zone will follow. According to the invention, the abovementioned catalytic gas-phase oxidation zones can be realized, for example, in separate reactors.

In other words, the catalytic gas-phase oxidation of the propene contained in the propane oxydehydrogenation product gas mixture to give an amount of acrolein predominating over that of acrylic acid can be carried out according to the invention, for example, as described in EP-A 731 082, DE-A 44 31 957, DE-A 29 09 597 or EP-A 575 897.

In other words, the gas-phase oxidation is effected in an expedient manner in a fixed-bed reactor having a multiplicity of catalyst tubes.

As a rule, a volume (1(S.T.P.)) ratio of propene to oxygen to essentially inert gases of 1: (1.0 to 3.0): (5 to 25), preferably 1: (1.7 to 2.3): (10 to 15), is employed.

To achieve the abovementioned ratios, it may be necessary additionally to introduce molecular oxygen into the propene-containing propane oxydehydrogenation product gas mixture before it is passed into the propene oxidation stage. This can be effected in the form of air, in the form of air depleted with respect to nitrogen or in the form of pure oxygen. Of course, additional diluent gases known to be essentially inert can be added at this point as desired. The reaction temperature is expediently chosen to be from 300 to 450° C., preferably from 320 to 390° C. The reaction pressure is usually from 0.5 to 5, preferably from 1 to 3, bar. The total space velocity is frequently from 1500 to 2500 l(S.T.P.) per l per h.

Suitable catalysts for this oxidation stage are, for example, those of DE-A 29 09 592, especially those of Example 1 of this publication. Alternatively, however, the multimetal oxide catalysts II or II' of DE-A 1 97 53 817 can also be used. This applies in particular to the embodiments by way of example, mentioned in these publications, especially when they are designed as unsupported hollow cylinder catalysts as described in EP-A 575 897. Of course, the Bi , Mo and Fe-containing multimetal oxide catalyst ACF-2 from Nippon Shokubai can also be used in the propene oxidation stage.

In the abovementioned propene oxidation stage, it is not pure acrolein that is obtained but a mixture from whose secondary components the acrolein can be separated in a manner known per se. The acrolein separated off in this manner can be used as an intermediate for the synthesis of various end products. Of course, it can also be used for the gas-phase catalytic oxidation for the preparation of acrylic acid. In a novel further use of the acrolein for the preparation of acrylic acid in a further gas-phase catalytic oxidation zone, the acrolein-containing reaction gases of the propene oxidation zone are transferred to this further oxidation zone without separation of secondary components. If necessary, they are cooled beforehand.

This further oxidation zone can be realized in an expedient manner likewise in a separate fixed-bed reactor having a multiplicity of catalyst tubes, as described, for example, in DE-A 44 31 949, DE-A 44 42 346, DE-A 1 97 36 105 or EP-A 731 082.

As a rule, a volume (l(S.T.P.)) ratio of acrolein to oxygen to steam to other essentially inert gases of 1:(1 to 3):(<0 to 20):(3 to 30), preferably 1:(1 to 3):(0.5 to 10):(7 to 18), is employed. To achieve the abovementioned ratios, it may be necessary additionally to introduce molecular oxygen into the acrolein-containing product gas mixture from the propene oxidation zone before it is passed into the acrolein oxidation zone. This can be effected in the form of air, in the form of air depleted with respect to nitrogen or in the form of pure oxygen. Of course, additional diluent gases known to be essentially inert may be added at this point as desired. The reaction temperature is expediently chosen to be from 200 to 300° C., preferably from 220 to 290° C. The reaction pressure is usually from 0.5 to 5, preferably from 1 to 3, bar. The total space velocity is preferably from 1000 to 2500 l(S.T.P.) per l per h. Suitable catalysts for this oxidation stage are, for example, those of the formula I or I' from DE-A 44 42 346. Alternatively, however, the multimetal oxide catalysts of DE-A 1 97 36 105, in particular the embodiments mentioned in this publication, can also be used. Of course, the Bi , Mo and Fe-comprising multimetal oxide catalyst ACS-4 from Nippon Shokubai can also be used in the acrolein oxidation stage.

According to the invention, it is essential that the various reaction zones described above can also be realized in a single reactor, as described, for example, in DE-A 19807079, i.e. the catalysts required for a catalytic oxydehydrogenation and the subsequent propene/acrolein oxidation can be realized, for example, within one and the same reaction tube as two or three successive catalyst beds (three successive catalyst zones). If the oxydehydrogenation is to be realized homogeneously, in the abovementioned arrangement the oxydehydrogenation catalyst bed can be replaced, for example, by an empty section in the reaction tube as the corresponding reaction zone. The individual catalyst beds and the empty section can be operated at one and the same temperature or, with a temperature-structured (multizone) reactor, at different temperatures.

The gas mixture leaving the acrolein oxidation zone does not of course consist of pure acrylic acid but of a gas mixture which contains the latter and from which acrylic acid can be separated in a manner known per se.

The various known methods for separating off acrylic acid are summarized, for example, in DE-A 1 96 00 955. It would also be possible for the separation of the acrolein from the reaction gas mixture leaving the propene oxidation zone to be effected in a corresponding manner. A common feature of the separation methods is that the desired product is separated from the reaction gas mixture of the acrolein oxidation stage either by absorption with a solvent (cf. also DE-A 43 08 087) or by absorption with water and/or partial condensation (the resulting absorbate or condensate is then worked up by distillation (with or without the addition of an azeotropic entraining agent) and/or by crystallization and essentially pure acrylic acid or pure acrolein is thus obtained).

In all cases, the separation line is drawn essentially so as to give a residual gas stream which is essentially free of acrylic acid and/or acrolein and for the most part free of $H_2O$ (as a rule, the $H_2O$ content of the residual gas stream is $\geq 10\%$ by volume) and whose main components are $N_2$ and unconverted propane. In addition, the residual gas stream may contain, for example, small amounts of gases such as carbon oxides (CO, $CO_2$), noble gases, $O_2$, $H_2O$ and unconverted propene.

The separation of at least a part of the nitrogen contained in the abovementioned residual gas stream, which is required according to the invention before said gas stream is further used as recycled gas, can be effected, for example, in a simple manner by distillation (it is of course possible to carry out nitrogen separation only in the case of a portion, for example from 50 to 70%, of the residual gas stream).

Expediently, fractional distillation is used, preferably fractional distillation under pressure at low temperatures. The pressure to be used may be, for example, from 10 to 100 bar. The rectification columns used may be packed columns or tray columns. Suitable tray columns are those having dual-flow trays, bubble trays or valve trays. The reflux ratio may be, for example, from 1 to 10. Other possibilities for separating off nitrogen are, for example, pressure-swing absorption, scrubbing under pressure and extraction under pressure.

The amount of nitrogen to be separated off according to the invention may be 5% or 10% or 20% or 30% or 40% or 50% or 60% or 70% or 80% or 90% or from 95 to 100%, based on the total amount of nitrogen contained in the residual gas stream.

It is of course also possible to separate the nitrogen from the residual gas stream not by itself but together with other components of the residual gas stream to be recycled, which components are less desirable when the novel process is carried out continuously. For example, the separation line in a separation of nitrogen from the residual gas stream by fractional distillation can be positioned so that, for example, essentially all those components whose boiling point is lower than the boiling point of propene are separated off at the top of the rectification column. These components are primarily the carbon oxides CO and $CO_2$ and unconverted oxygen and ethylene as well as methane. Of course, it is also possible for only part of the abovementioned components to be separated off together with nitrogen. Preferably, the novel process is carried out in such a way that at least 70%, preferably at least 80%, of the molecular oxygen fed altogether to the various reaction zones have been converted by the time when the product gas mixture leaves the last reaction zone.

EXAMPLES

A) Preparation of Acrolein and/or Acrylic Acid Starting from Propane a) 26.8 mol/h of a gas mixture (modified air) consisting of 90% by volume Of $O_2$ and 10% by volume of $N_2$ plus 71.9 mol/h of recycled gas in the composition, 96.2% by volume of propane, 0.4% by volume of propene, 2.9% by volume of $H_2O$, 0.1% by volume Of $CO_2$ and 0.4% by volume of other components were combined to give 98.7 mol/h of reaction gas starting mixture, compressed to 2.5 bar and heated to 430° C. A 6.8 m long reaction tube of V2A stainless steel (2.5 mm wall thickness, 2.6 cm internal diameter) which was cooled to 430° C. over its entire length in a salt bath was fed with the abovementioned reaction gas starting mixture. In the direction of flow, the reaction tube was loaded first over a bed length of 0.8 mm with a spherical (diameter=8 mm) steatite moldings (instead of steatite beads, bed comprising rings measuring 5 mm×3 mm×2 mm=external diameter×height× internal diameter may also be used here) and then over a bed length of 3.0 m with a bed of the multimetal oxide catalyst of Example 1, a)/multimetal oxide material I according to DE-A 19753817, molded to give unsupported catalyst in the form of cylinders measuring 5 mm×3 mm×2 mm (external diameter×height×internal diameter), and subsequently over a bed length of 3 m with a bed of the multimetal oxide catalyst according to Example 1,3/multi-metal oxide II from DE-A 19753817. The inlet pressure was 2.5 bar and the outlet pressure 1.9 bar. The product gas mixture leaving the reaction tube (106.1 mol/h) had the following composition:

5.2% by volume of acrolein, 0.4% by volume of acrylic acid, 57.0% by volume of propane, 0.3% by volume of propene, 4.0% by volume of $O_2$, 2.6% by volume of $N_2$, 22.8% by volume of $H_2O$, 3.9% by volume of Co, 3.5% by volume of $CO_2$ and 0.3% by volume of other components.

2.4 mol/h of a gas mixture (modified air) consisting of 90% by volume of $O_2$ and 10% by volume of $N_2$ were mixed with the abovementioned product gas mixture to give a reaction gas starting mixture having the following composition:

5.1% by volume of acrolein, 0.4% by volume of acrylic acid 55.7% by volume of propane, 0.3% by volume of propene, 5.9% by volume of $O_2$, 2.8% by volume of $N_2$, 22.3% by volume of $H_2O$, 3.8% by volume of CO, 3.4% by volume of $CO_2$ and 0.3% by volume of other components.

The reaction gas starting mixture was brought to 200° C. and used for loading the following acrolein oxidation tube.

This reaction tube (V2A stainless steel, length 3.80 m, 2.0 mm wall thickness, 2.6 cm internal diameter) was loaded, in the outflow direction, first with an initial bed of steatite beads (diameter 4–5 mm) over a length of 50 cm. This was followed over a catalyst tube length of 2.70 m by a bed of the multimetal oxide catalyst according to Example b, S1 of DE-A 4442346. The reaction tube was kept at 270° C. over its entire length by means of a salt bath and fed with the reaction gas starting mixture described above. The inlet pressure was 1.9 bar and the outlet pressure was 1.7 bar. The product mixture leaving the reaction tube in an amount of 106.0 mol/h had the following composition:

0.1% by volume of acrolein, 5.2% by volume of acrylic acid, 0.1% by volume of acetic acid, 57.1% by volume of propane, 0.3% by volume of propene, 3.0% by volume of $O_2$, 2.8% by volume of $N_2$, 23.1% by volume of $H_2O$, 4.1% by volume of CO, 3.9% by volume of $CO_2$ and 0.3% by volume of other components.

The hot reaction gas leaving the acrolein oxidation stage was cooled to about 175° C. in a Venturi scrubber (quench apparatus) by direct contact with quench liquid (140–150° C.) which was sprayed through slots located in the region of the narrowest cross-section of the Venturi tube and which comprised 57.4% by weight of diphenyl ether, 20.7% by weight of diphenyl and 20% by weight of o-dimethyl phthalate. Thereafter, the amount of the quench liquid remaining as liquid droplets was separated, in a downstream drop separator (receiver having a gas tube leading upward), from the gas phase consisting of reaction gas and vaporized quench liquid, and was recycled in a circulation I to the Venturi scrubber. A part-stream of the recycled quench liquid was subjected to a solvent distillation, the quench liquid being distilled over and high-boiling secondary components remaining behind and being incinerated. The quench liquid which was distilled over was fed to the discharge of the absorption column described below.

The gas phase having a temperature of about 175° C. was fed to the lower part of a packed absorption column (3 m high, double glass jacket, internal diameter 50 mm, three packing zones having the length (from bottom to top) of a 90 cm, 90 cm and 50 cm, the packing zones were thermostated as follows from bottom to top: 90° C., 60° C., 20° C., the penultimate and the final packing zones were separated by a chimney tray, the packings were metal helices of stainless steel having a helix diameter of 5 mm and a helix length of 5 mm; the absorbent was fed in directly above the middle packing zone) and was exposed to the countercurrent of 2400 g/h of the absorbent likewise composed of 57.4% by weight of diphenyl ether, 20.7% by weight of diphenyl and 20% by weight of o-dimethyl phthalate and having a temperature of 50° C. Discharge of the absorption column, which, in addition to acrylic acid, also contained absorbed lower boiling byproducts, such as acrolein and acetic acid, was heated indirectly to 100° C. in a heat exchanger and fed to the top of a desorption column, which was likewise in the form of a packing column having a length of 2 m (double glass jacket, 50 mm internal diameter, packings: stainless steel helices having each a helix diameter of 5 mm and a helix length of mm, one packing zone having a length of 1 m, thermostated at 120° C.). In the desorption column, the components having a lower boiling point than acrylic acid, such as acrolein and acetic acid, were substantially removed from the acrylic acid/absorbent mixture by stripping with 9.1 mol/h of propane (countercurrent, feed temperature 120° C.). The laden propane (stripping gas) leaving the desorption column was recirculated and was combined with the hot reaction gas from the acrolein oxidation stage before its entry into the Venturi quench.

The unabsorbed gas mixture leaving the second packing zone in an upward direction in the absorption column was further cooled in the third packing zone in order to separate off the readily condensable part of the secondary components contained therein, e.g. water and acetic acid, by condensation. This condensate is referred to as dilute acid solution. To increase the separation effect, a part of the dilute acid solution was recycled to the absorption column above the third packing zone of the absorption column at a temperature of 20° C. The dilute acid solution was removed below the top packing zone, from the chimney tray located there. The reflux ratio was 200. The continuously removed amount of dilute acid solution was 22.8 mol/h. In addition to 94.5% by weight of water, it also contained 2.8% by weight of acrylic acid. This can, if required, be recovered as described in DE-A 1 96 00 955. The gas stream which is the last to leave the absorption column formed the residual gas stream.

The bottom liquid of the desorption column was fed to the 8th tray from the bottom of a tray column containing 57 dual-flow trays (internal diameter 50 mm, length 3.8 m; top pressure 100 mbar, bottom pressure 280 mbar, bottom temperature 195° C., the resistance to pressure loss was mounted on the 9th tray) and was rectified in said tray column. 5.3 mol/hour of a crude acrylic acid were removed from the 48th tray from the bottom, via a side take-off. The purity of the crude acrylic acid removed was ≧98% by weight. After a partial condensation (reflux ratio 8.7), a gas stream enriched in low boilers and containing acrylic acid was taken off at the top of the rectification column and was recycled to the absorption column, above the bottom packing zone. The absorbent which was free of low boilers and virtually free of acrylic acid was taken off from the bottom of the rectification column and recycled to the absorption column, above the second packing zone (viewed from below). Phenothiazine as a polymerization inhibitor was added to the reflux at the top of the rectification column, in amounts such that the side take-off contained 300 ppm of phenothiazine (a schematic diagram of the working-up process for the reaction gas of the acrolein oxidation stage is shown in DE-A 1 96 00 955; in addition, the working-up procedure is also described in DE-A 4308087).

The residual gas stream leaving the absorption column had the following composition:

80.1% by volume of propane,
0.4% by volume of propene,
3.6% by volume of $O_2$,
3.4% by volume of $N_2$,
2.4% by volume of $H_2O$,
5.0% by volume of CO,
4.7% by volume of $CO_2$ and
0.4% by volume of other components.

Its amount was 87.0 mol/h. It was compressed at 36 bar, cooled to 70° C. and then fed to a rectification column which was operated under pressure and had 51 trays. The residual gas stream was fed in to the 30th tray from the bottom. The top pressure of the rectification column (a bubble tray column, diameter 50 mm) was 36 bar. The top of the column was cooled with the coolant Baysilone® KT3 (feed temperature −50° C.). The bottom temperature was 92° C. A part of the bottom liquid removed was recycled as vapor to the bottom of the column. At the top of the column, 15.1 mol/h of a waste gas which had the following composition:

26.8% by volume of $CO_2$,
28.7% by volume of CO,
3.5% by volume of propane,
19.6% by volume of $N_2$,
21.0% by volume of $O_2$,
0.2% by volume of propene and
0.2% by volume of other components were thus removed at the top of the column. The continuously removed bottom liquid amounted to 71.9 mol/h. It was converted into the vapor phase and was recycled as recycled gas to the catalytic propene oxydehydrogenation, as described at the outset.

The yield of acrylic acid was 58.4 mol %, based on the amount of propane used, and the selectivity of the acrylic acid was 62.2 mol %. The oxygen conversion was 87.9 mol %, based on the total amount of oxygen used.

Finally, it should be noted that, according to the invention, recycled gas, too, can be used instead of propane for stripping. In this case, the required propane can be fed, for example, directly to the oxydehydrogenation stage.

b) 35.3 mol/h of a gas mixture (modified air) consisting of 90% by volume of $O_2$ and 10% by volume of $N_2$ and 137.8 mol/h of recycled gas having the composition 96.1% by volume of propane,
0.4% by volume of propene,
3.0% by volume of $H_2O$,
0.1% by volume of $CO_2$ and
0.4% by volume of other components, were combined to give 173.1 mol/h of reaction gas starting mixture, compressed to 1.8 bar and heated to 430° C. A 3.8 m long reaction tube of V2A stainless steel (2.0 mm wall thickness, 2.6 cm internal diameter) which was cooled over its total length to 430° C. in a salt bath was fed with the abovementioned reaction gas starting mixture.

In the direction of flow, the reaction tube was loaded over a length of 0.8 m first with spherical (diameter=8 mm) steatite moldings (instead of the steatite beads, the steatite rings having the geometry mentioned below and measuring 5 mm×3 mm×2 mm may also be used here).

Over the remaining bed length of 3 m, the reaction tube was filled with a bed of the multimetal oxide catalyst according to Example 1,a)/multimetal oxide material I of DE-A 19753817, molded to give unsupported catalyst cylinders measuring 5 mm×3 mm×2 mm (external diameter×height×internal diameter). The inlet pressure was 1.8 bar, the outlet pressure was 1.3 bar. The product mixture leaving the reaction tube (186.7 mol/h) had the following composition:

0.2% by volume of acrolein,
62.1% by volume of propane,
6.7% by volume of propene,
4.8% by volume of $O_2$,
2.0% by volume of $N_2$,
17.4% by volume of $H_2O$,
3.8% by volume of CO,
2.7% by volume of $CO_2$ and
0.3% by volume of other components.

15.9 mol/h of a gas mixture consisting of 90% by volume of $O_2$ and 10% by volume of $N_2$ were mixed with the abovementioned product mixture compressed to 2.4 bar, giving, for the following gas-phase catalytic propene oxidation, a reaction gas starting mixture which had the following composition:

0.2% by volume of acrolein,
57.1% by volume of propane,
6.2% by volume of propene,
11.5% by volume of $O_2$,
2.6% by volume of $N_2$,
16.1% by volume of $H_2O$,
3.8% by volume of CO,
2.5% by volume of $CO_2$ and
0.3% by volume of other components.

A reaction tube (V2A stainless steel, length 3.8 m, 2.0 mm wall thickness, 2.6 cm internal diameter) was loaded, in the outflow direction, first with a preliminary bed of steatite beads (diameter 4–5 mm) over a length of 50 cm. This was followed, over a catalyst tube length of 3.0 m, by a bed of the multimetal oxide catalyst according to Example 1,3./multimetal oxide II from DE-A 19753817. The reaction tube was kept at 350° C. over its total length by means of a salt bath and fed with 202.6 mol/h of the abovementioned reaction gas starting mixture (which had a temperature of 200° C.). The outlet pressure was 2.0 bar.

4.7 mol/h of a gas mixture consisting of 90% by volume of $O_2$ and 10% by volume of $N_2$ were mixed with the product gas mixture leaving the reaction tube of the propene oxidation stage, and the acrolein oxidation tube described below was fed with the resulting reaction gas starting mixture, which had been brought to 200° C.

This reaction tube (V2A stainless steel, length 3.80 m, 2.0 mm wall thickness, 2.6 cm internal diameter) was loaded, in the outflow direction, first with a preliminary bed of steatite beads (diameter 4–5 mm) over a length of 50 cm. This was followed over a catalyst tube length of 2.70 m by a bed of the multimetal oxide catalyst according to Example b, S1 of DE-A 4442346. The reaction tube was kept at 270° C. over its total length by means of a salt bath and fed with the reaction gas starting mixture described above. The inlet pressure was 1.9 bar and the outlet pressure was 1.7 bar. The product gas mixture leaving the reaction tube in an amount of 203.1 mol/h had the following composition:

0.1% by volume of acrolein,
5.2% by volume of acrylic acid,
0.1% by volume of acetic acid,
57.0% by volume of propane,
0.3% by volume of propene,
3.0% by volume of $O_2$,
2.8% by volume of $N_2$,
23.2% by volume of $H_2O$,
4.1% by volume of Co,
3.9% by volume of $CO_2$ and
0.3% by volume of other components.

The acrylic acid formed was separated, in a manner corresponding to that in A a), from the hot reaction gas leaving the acrolein oxidation stage. 17.4 mol/h of propane were used for stripping.

The amount of dilute aqueous acid separated off was 43.6 mol/h. It contained 94.2% by weight of water and 3.1% by weight of acrylic acid. The amount of crude acrylic acid separated off in the rectification column via the side take-off was 10.2 mol/h.

The residual gas stream leaving the absorption column had the following composition:

80.0% by volume of propane,
0.4% by volume of propene,
3.6% by volume of $O_2$,
3.4% by volume of $N_2$,
2.5% by volume of $H_2O$,
5.0% by volume of CO,
4.7% by volume of $CO_2$ and
0.4% by volume of other components.

Its amount was 166.7 mol/h. 29.0 mol/h of waste gas having the following composition 3.6% by volume of propane,
21.0% by volume of $O_2$,
19.6% by volume of $N_2$,
28.7% by volume of CO,
0.2% by volume of propene,
26.8% by volume of $CO_2$ and
0.2% by volume of other components, were separated, as described in Aa), from this residual gas stream before the remaining residual gas stream was recycled to the oxydehydrogenation as recycled gas in the manner described. Finally, it should be noted that, according to the invention, recycled gas can also be used for stripping instead of propane. In this case, the required propane can be fed, for example, directly to the oxydehydrogenation stage.

The yield of acrylic acid was 58.5 mol %, based on the amount of propane used. The selectivity of the acrylic acid formation was 62.4 mol % and the total oxygen conversion was 87.9 mol %.

c) 15.4 mol/h of a gas mixture (modified air) consisting of 90% by volume of $O_2$ and 10% by volume of $N_2$ and 82.9 mol/h of recycled gas having the composition 97.4% by volume of propane,
0.4% by volume of propene,
0.2% by volume of ethene,
1.3% by volume of $H_2O$, 0.1% by volume of $CO_2$ and 0.6% by volume of other components were combined to give 98.3 mol/h of reaction gas starting mixture, compressed to 1.8 bar and heated to 430° C. An empty reaction tube of V2A stainless steel (2.0 mm wall thickness, 2.6 cm internal diameter) which was heated to 513° C. over its total length (electrical heating tape) was fed with the abovementioned reaction starting mixture. The tube length was such that the average residence time in the tube was 3 seconds. The product mixture leaving the reaction tube (107.0 mol/h) had the following composition:

65.0% by volume of propane, 7.0% by volume of propene, 1.3% by volume of ethene, 0.5% by volume of methane, 2.0% by volume of $O_2$, 1.5% by volume of $N_2$, 16.5% by volume of $H_2O$, 2.8% by volume of CO, 2.3% by volume of $CO_2$ and 1.1% by volume of other components.

13.0 mol/h of a gas mixture consisting of 90% by volume of $O_2$ and 10% by volume of $N_2$ were mixed with the abovementioned product mixture, giving, for the following gas-phase catalytic propene oxidation, a reaction gas starting mixture which had the following composition:

58.0% by volume of propane, 6.3% by volume of propene, 1.1% by volume of ethene, 0.4% by volume of methane, 11.5% by volume of $O_2$, 2.4% by volume of $N_2$, 14.7% by volume of $H_2O$, 2.5% by volume of CO, 2.0% by volume of $CO_2$ and 1.1% by volume of other components.

A reaction tube (V2A stainless steel, length 3.80 m, 2.0 mm wall thickness, 2.6 cm internal diameter) was loaded, in the outflow direction, first with a preliminary bed of steatite beads (diameter 4–5 mm) over a length of 50 cm. This was followed over a catalyst tube length of 3.00 m by a bed of the multimetal oxide catalyst according to Example 1,3./ multimetal oxide II from DE-A 19753817. The reaction tube was kept at 350° C. over its total length by means of a salt bath and fed with 120.0 mol/h of the abovementioned reaction gas starting mixture which had been compressed to 1.8 bar (and had a temperature of 200° C.). The outlet pressure was 1.6 bar.

2.8 mol/h of a gas mixture consisting of 90% by volume of $O_2$ and 10% by volume of $N_2$ were mixed with the product gas mixture leaving the reaction tube of the propene oxidation stage, and the acrolein oxidation tube described below was fed with the resulting reaction gas starting mixture, which had been brought to 200° C.

This reaction tube (V2A stainless steel, length 3.80 m, 2.0 mm wall thickness, 2.6 cm internal diameter) was loaded, in the outflow direction, first with a preliminary bed of steatite beads (diameter 4–5 mm) over a length of 50 cm. This was followed over a catalyst tube length of 2.70 m by a bed of the multimetal oxide catalyst according to Example b, S1 of DE-A 4442346. The reaction tube was kept at 270° C. over its total length by means of a salt bath and fed with the reaction gas starting mixture described above. The inlet pressure was 1.5 bar and the outlet pressure was 1.3 bar. The product mixture leaving the reaction tube in an amount of 120.3 mol/h had the following composition:

0.1% by volume of acrolein, 5.3% by volume of acrylic acid, 0.3% by volume of acetic acid, 57.3% by volume of propane, 0.3% by volume of propene, 1.3% by volume of ethene, 0.5% by volume of methane, 3.0% by volume of $O_2$, 2.7% by volume of $N_2$, 21.8% by volume of $H_2O$, 3.0% by volume of CO, 3.4% by volume of $CO_2$ and 1.0% by volume of other components The acrylic acid formed was separated, in a manner corresponding to that in Aa), from the hot reaction gas leaving the acrolein oxidation stage. 12.1 mol/h of propane were used for stripping.

The amount of dilute aqueous acid separated off was 25.8 mol/h. It contained 94.4% by weight of water and 2.9% by weight of acrylic acid. The amount of crude acrylic acid separated off in the rectification column via the side take-off was 6.2 mol/h.

The residual gas stream leaving the absorption column had the following composition:

80.9% by volume of propane, 0.4% by volume of propene, 1.5% by volume of ethene, 0.6% by volume of methane, 3.6% by volume of $O_2$, 3.2% by volume of $N_2$, 1.1% by volume of $H_2O$, 3.6% by volume of CO, 4.0% by volume of $CO_2$ and 1.1% by volume of other components.

Its amount was 100.2 mol/h. 17.3 mol/h of waste gas having the following composition:

1.8% by volume of propane, 0.1% by volume of ethane, 0.2% by volume of propene, 8.0% by volume of ethene, 3.4% by volume of methane, 20.6% by volume of $O_2$, 18.5% by volume of $N_2$, 20.6% by volume of CO, 22.8% by volume of $CO_2$ and 4.2% by volume of other components were separated, as described in Aa), from this residual gas stream before the remaining residual gas stream was recycled as recycled gas to the oxydehydrogenation in the manner described. Finally, it should be noted that, according to the invention, recycled gas can also be used for stripping instead of propane. In this case, the required propane can be fed, for example, directly to the oxydehydrogenation stage. The yield of acrylic acid was 51.4 mol %, based on the amount of propane used. The selectivity of the acrylic acid formation was 52.9 mol % and the total oxygen conversion was 87.3 mol %.

B) Preparation of 1 mol/s of acrylic acid (20° C., 1 bar) by combination of propane oxydehydrogenation and cata- lytic gas-phase oxidation—consideration of the separation work to be performed for separating off nitrogen (to simplify the consideration, a 50% conversion of the propane in the oxydehydrogenation and complete conversion in the gas-phase oxidation and 100% selectivity of the respective desired compound will be assumed here).

a) Use of pure $O_2$ as oxygen source

The stoichiometry of the oxydehydrogenation reaction of propane to propene is:

The stoichiometry of the catalytic gas-phase oxidation reaction of propene to acrylic acid is:

Accordingly, 2.0 mol/s of $O_2$ are required for producing 1 mol/s of acrylic acid by oxydehydrogenation of propane and subsequent gas-phase oxidation of propene (under the abovementioned conditions). The starting material for obtaining 2.0 mol/s of $O_2$ is air (78% by volume of $N_2$, 21% by volume of $O_2$ and 1% by volume of remaining gases) whose composition, for the sake of simplicity, is to be assumed as 80% by volume of $N_2$ and 20% by volume of $O_2$. Furthermore, ideal behavior is to be assumed. Accordingly, to obtain 2.0 mol/s of $O_2$, it is possible to start from 10.0 mol/s of air (=a mixture of 8.0 mol/s of $N_2$ and 2.0 mol/s of $O_2$) which has a temperature of 20° C. and a pressure of 1 bar.

In order to separate 2.0 mol/s of pure $O_2$ from the abovementioned 10.0 mol/s of air, the air is cooled to −194° C. while maintaining the pressure of 1 bar and is fed, as liquid in the boiling state, to the middle part of a rectification column operated adiabatically at 1 bar, in order to be separated into pure nitrogen via the top and into pure oxygen as a bottom liquid.

In order to realize this required separation of the mixture, according to K. Sattler, thermische Trennverfahren, Grundlagen, Auslegung, Apparate, second edition, Verlag Chemie, Weinheim (1995), page 182, a minimum reflux ratio is required at the top of the column when an ideal rectification column, i.e. one having an infinite number of theoretical plates, is used (the greater the required minimum reflux ratio, the greater is the separation work to be performed).

While the reflux ratio at the top of the column for a given separation problem is defined very generally as the ratio of that fraction of the amount of $N_2$ obtained in gaseous form at the top of the rectification column per unit time which is recycled to the rectification column after condensation to the fraction which is removed, the minimum reflux ratio at the top of the column ($v_{min}$) is defined as the ratio of that minimum fraction of the amount of $N_2$ obtained in gaseous form at the top of the rectification column per unit time which must be recycled after condensation to the rectification column to realize the set separation task to the fraction which is removed. According to the abovementioned citation by K. Sattler:

$$v_{min} = \frac{1}{\alpha - 1}\left[\frac{X^E}{X^F} - \alpha\frac{1 - X^E}{1 - X^F}\right]$$

with
$\alpha$=is the relative volatility of separation factor of $N_2$ and $O_2$ (i.e. the ratio of the saturation vapor pressures of $N_2$ and $O_2$ at the mean separation temperature along the rectification column (the separation of the mixture takes place along the total rectification column)).

The boiling point of $N_2$ at 1 bar is −196° C. (=top temperature). The boiling point of $O_2$ at 1 bar is −183° C. (=bottom temperature). Thus, the mean boiling point along the rectification column is −190° C. According to VDI Heat Atlas, 5th Edition 1998 (DC6 and DC7), the saturation vapor pressure of $N_2$ at −190° C. is 2.0 bar and the saturation vapor pressure of $O_2$ at −190° C. is 0.48 bar. The relevant a is thus 2.0:0.48=4.15.

$X^F$ is the molar $N_2$ fraction of the mixture (i.e. of air) fed to the rectification column and to be separated, i.e. $X^F$=0.8 (=80% by volume of $N_2$ in air).

$X^E$ is the molar $N_2$ fraction in the top take-off. Since pure nitrogen is to be separated off at the top, $X^E$=1.

Thus, $v_{min}$ is 0.4, i.e. 3.2 mol/s of $N_2$ must be recycled to the column in order to be able to remove 8 mol/s of pure $N_2$ at the top of the column.

Altogether, 11.2 mol/s of liquid $N_2$ are thus fed to the column per unit time (8.0 mol/s as a component of the liquid air and 3.2 mol/s as reflux at the top of the column), the total amount of which must be vaporized continuously. To vaporize this amount of liquid, a corresponding amount of liquid must be recycled as vapor to the bottom of the column. At the same time, 2.0 mol/s Of $O_2$ are removed at the bottom of the column.

Figure 1:
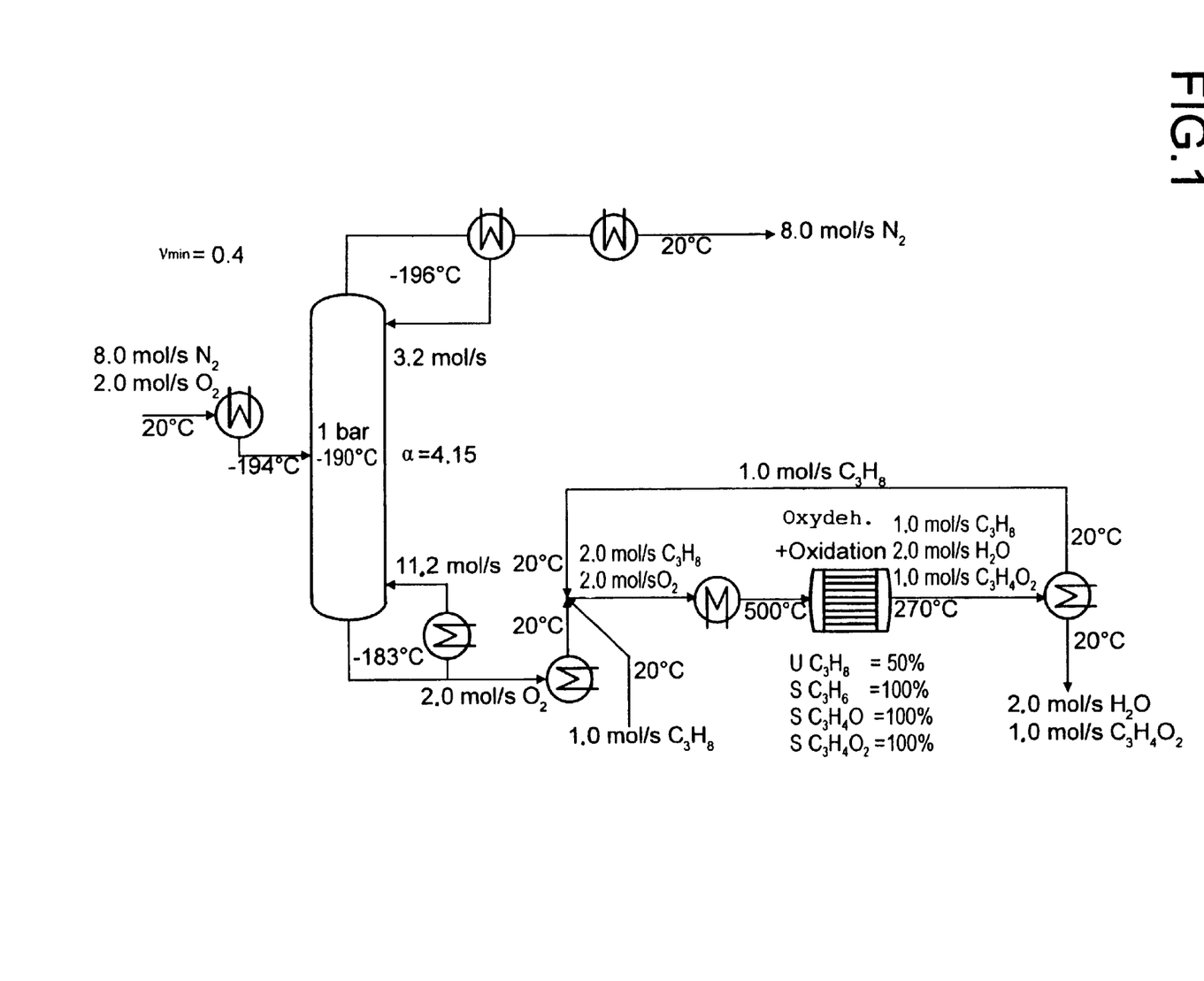
FIGS. 1 and 2 give overviews of the routes described in the examples.

The oxygen removed in liquid form at the bottom of the column is heated to 20° C. at 1 bar, mixed with 2 mol/s of propane (20° C., 1 bar), heated to 500° C. while maintaining the pressure of 1 bar and subjected to oxydehydrogenation (either catalytically and/or homogeneously) and then subjected to gas-phase catalytic oxidation. The reaction gas mixture consisting of 1 mol/s of propene, 2 mol/s of $H_2O$ and 1.0 mol/s of acrylic acid is then cooled to 20° C. while maintaining the pressure, the water vapor and the acrylic acid condensing completely owing to the large boiling point difference and 1 mol/s of pure propane (1 bar, 20° C.) being obtained and being recycled to the oxydehydrogenation. FIG. 1 gives an overall view of the above b) Use of a mixture of 80% by volume of $O_2$ and % by volume of $N_2$ To obtain the mixture mentioned in the heading, 10 mol/s of air (a mixture of 2.0 mol/s of $O_2$ and 8.0 mol/s of $N_2$) is used as a starting material, said air having a temperature of 20° C. and a pressure of 1 bar. This is separated in a first rectification column.

The separation by rectification is effected as in a), but into pure nitrogen (top product) and a mixture of 80% by volume of $O_2$ and 20% by volume of $N_2$ (bottom product).

The boiling point of $N_2$ at 1 bar is −196° C. (=top temperature). The boiling point of a mixture of 80% by volume of $O_2$ and 20% by volume of $N_2$ at 1 bar is −187° C. (=bottom temperature). The mean boiling point along the rectification column is thus −192° C.

According to VDI Heat Atlas, 5th edition 1998 (DC6 and DC7), the saturation vapor pressure of $N_2$ at −192° C. is 1.615 bar and the saturation vapor pressure of $O_2$ is 0.37 bar. The relevant $\alpha$ is thus 1.615:0.37=4.36.

$X^F$ is the molar $N_2$ fraction in the mixture fed to the rectification column and to be separated (i.e. in air), i.e. $X^F$=0.8 (=80% by volume of $N_2$ in air). $X^E$ is the molar $N_2$ fraction in the top take-off. Since it is intended to separate off pure nitrogen at the top, $X^E$=1. Thus, $v_{min}$ is 0.37, i.e.

2.78 mol/s of $N_2$ must be recycled in liquid form to the column in order to be able to remove 7.5 mol/s of pure $N_2$ at the top of the column. Altogether, 10.28 mol/s of liquid $N_2$ are thus fed to the column per unit time (8.0 mol/s as a component of the liquid air and 2.78 mol/s at the top of the column), of which the sum of 7.5 mol/s (the take-off at the top) and 2.78 mol/s (the reflux amount) must be vaporized per unit time. In order to vaporize this amount of liquid, a corresponding amount of liquid must be recycled in vapor form to the bottom of the column. At the same time, a mixture of 2.0 mol/s of $O_2$ (80% by volume) and 0.5 mol/s of $N_2$ (20% by volume) is removed continuously from the bottom of the column. The mixture of 2.0 mol/s of $O_2$ and 0.5 mol/s of $N_2$ thus obtained is heated to 20° C. while maintaining the pressure of 1 bar and is mixed with 2.0 mol/s of propane, which likewise has a pressure of 1 bar. The mixture is heated to 500° C. while maintaining the pressure and, under these conditions, is subjected to catalytic and/or homogeneous oxydehydrogenation and subsequently to gas-phase catalytic oxidation.

The resulting reaction product mixture is cooled to 20° C. while maintaining the pressure of 1 bar, the water of reaction and the acrylic acid condensing completely as a result of the large boiling point difference. The remaining mixture which is at 20° C. and 1 bar and comprises 1.0 mol/s of propane and 0.5 mol/s of $N_2$ is cooled (−185° C.) while maintaining the pressure until it can be fed as a boiling liquid to the middle part of a second rectification column operated adiabatically at 1 bar, in order to be separated into pure nitrogen via the top and into pure propane as a bottom liquid.

The boiling point of $N_2$ at 1 bar is −196° C. (=top temperature). The boiling point of propane at 1 bar is −42° C. (=bottom temperature).

The mean boiling point along the rectification column is thus −119° C. According to VDI Heat Atlas, 5th edition 1998 (DC6 and DC7), the saturation vapor pressure of $N_2$ at −119° C. is 104.9 bar and the saturation vapor pressure of propane at −119° C. is 0.0045 bar. The a relevant in the second rectification column is thus 104.9:0.0045=23,300. $X^F$ is the molar $N_2$ fraction in the mixture fed to the rectification column and to be separated, i.e. $X^F$=0.5/1.5=0.33. $X^E$ is the molar $N_2$ fraction in the top take-off. Since it is intended to separate off pure nitrogen at the top, $X^E$=1. Thus, $v_{min}$ is 0.00013, i.e. only 0.000064 mol/s of $N_2$ must be recycled in liquid form to the column in order to be able to remove 0.5 mol/s of $N_2$ at the top of the column.

Altogether, 0.500064 mol/s of liquid $N_2$ are thus fed to the column per unit time (0.5 mol/s as a component of the liquid mixture fed in and 0.000064 mol/s at the top of the column), the total amount of which must be vaporized continuously.

In order to vaporize this amount of liquid, a corresponding amount of liquid in vapor form must be recycled to the bottom of the column. At the same time, 1.0 mol/s of propane is removed from the bottom of the column, heated to 20° C. while maintaining the pressure (1 bar) and recycled to the oxydehydrogenation.

Figure 2:
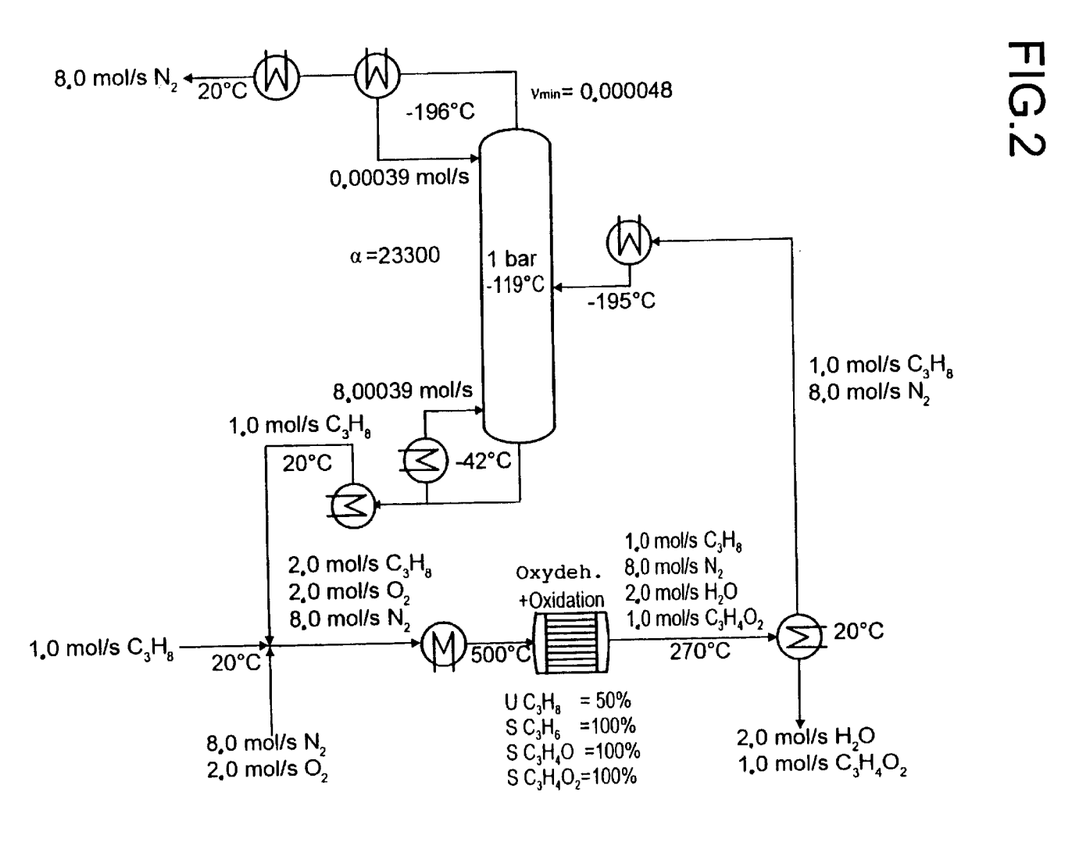

FIG. 2 gives an overview of the above. If the routes a) and b) are compared with one another, the lower $v_{min}$ in case b) ($\Sigma v_{min}$=0.37+0.00013=0.37013) in contrast to $v_{min}$=0.4 in case a) shows that less separation work has to be performed when air only partially depleted with respect to nitrogen is used.

We claim:

1. A process for the preparation of acrolein, acrylic acid or the combination of acrolein and acrylic acid from propane, in which, in a first reaction zone, the propane is subjected to a partial oxydehydrogenation with molecular oxygen under homogeneous catalysis, heterogeneous catalysis or the combination of homogeneous and heterogeneous catalysis to give propene, and the propene-containing product gas mixture formed in the first reaction zone is fed, without separating off a component of the product gas mixture, into at least one further reaction zone and, in this at least one further reaction zone, the propene contained in the product gas mixture of the first reaction zone, together with all components of the product gas mixture of the first reaction zone, is subjected to a gas-phase catalytic oxidation to acrolein, acrylic acid or the combination of acrolein and acrylic acid, acrolein, acrylic acid or the combination of acrolein and acrylic acid and water contained in the product gas mixture of the gas-phase catalytic oxidation are separated from said mixture, and the unconverted propane contained in the remaining residual gas stream is recycled as a component of the residual gas stream to the first reaction zone, wherein the molecular oxygen required in the first reaction zone and differing from recycled oxygen is added as nitrogen-containing modified air to the reaction gas starting mixture fed to the first reaction zone, with the proviso that the nitrogen content of the modified air is less than, and the oxygen content of the modified air greater than, the corresponding contents of air, and, before the recycling of the residual gas stream to the first reaction zone, at least a part of the molecular nitrogen contained in the residual gas stream is separated from the residual gas stream.

2. A process as claimed in claim 1, wherein, before the recycling of the residual gas stream to the first reaction zone, the total amount of the molecular nitrogen contained in the residual gas stream is separated from the residual gas stream.

3. A process as claimed in claim 1, wherein nitrogen is separated off by fractional distillation.

4. A process as claimed in claim 3, wherein all components of the residual gas stream which have a boiling point lower than that of propene are separated off together with the nitrogen.

5. The process as claimed in claim 1, wherein the partial oxydehydrogenation is carried out under homogeneous catalysis at a temperature of 300 to 700° C.

6. The process as claimed in claim 1, wherein the partial oxydehydrogenation is carried out under homogeneous catalysis at a temperature of 400 to 600° C.

7. The process as claimed in claim 1, wherein the partial oxydehydrogenation is carried out under homogeneous catalysis at an operating pressure of 0.5 to 100 bar.

8. The process as claimed in claim 1, wherein the partial oxydehydrogenation is carried out under homogeneous catalysis and the propane is present in a reaction gas mixture and a residence time of the reaction gas mixture ranges from 0.1 to 20 seconds.

9. The process as claimed in claim 1, wherein the partial oxydehydrogenation is carried out under homogeneous catalysis, and wherein a propane to oxygen ratio ranges from 0.5:1 to 40:1.

10. The process as claimed in claim 1, wherein the partial oxydehydrogenation is carried out under homogeneous catalysis wherein a molar ratio of propane to molecular oxygen is ≦6:1.

11. The process as claimed in claim 1, wherein the propane and molecular oxygen are present together in a reaction gas starting mixture which optionally further comprises one or more inert components selected from the group consisting of $H_2O$, $CO_2$, CO, $N_2$, noble gases, and propene.

12. The process as claimed in claim 1, wherein the partial oxydehydrogenation is carried out over a catalyst having the formula I:

$$M^1{}_a Mo_{1-b} M^2{}_b O_x \qquad (1)$$

wherein:

$M^1$ is Co, Ni, Mg, Zn, Mn and/or Cu, $M^2$ is W, V, Te, Nb, P, Cr, Fe, Sb, Ce, Sn, and/or La, a is from 0.5 to 1.5, bis from 0 to 0.5, and x is a number which is determined by the valency and frequency of the elements other than oxygen in the formula I.

13. The process as claimed in claim 1, wherein the partial oxydehydrogenation is carried out under heterogeneous catalysis at a temperature of 300 to 600° C.

14. The process as claimed in claim 1, wherein the partial oxydehydrogenation is carried out under heterogeneous catalysis at a temperature of 350 to 500° C.

15. The process as claimed in claim 1, wherein the partial oxydehydrogenation is carried out under heterogeneous catalysis at an operating pressure of 0.5 to 10 bar.

16. The process as claimed in claim 1, wherein the partial oxydehydrogenation is carried out under heterogeneous catalysis and wherein a propane and oxygen ratio ranges from 0.5:1 to 40:1.

17. The process as claimed in claim 1, wherein the partial oxydehydrogenation is carried out under heterogeneous catalysis at a molar ratio of propane to molecular oxygen of $\leq 6:1$.

18. The process as claimed in claim 1, wherein modified air is used as an oxygen source in the partial oxydehydrogenation, and wherein the modified air has a nitrogen content of $\geq 1$ to $\leq 70\%$ by volume.

19. The process as claimed in claim 1, wherein modified air is used as an oxygen source in the partial oxydehydrogenation, and wherein the modified air has an oxygen content ranging from >20.95 to 99.95% by volume.

20. The process as claimed in claim 1, wherein, before the recycling of the residual gas stream to the first reaction zone, 5% to 100% of the molecular nitrogen contained in the residual gas stream is separated from the residual gas stream.

* * * * *